US009320441B1

(12) United States Patent
Hays (10) Patent No.: US 9,320,441 B1
(45) Date of Patent: Apr. 26, 2016

(54) MEDICAL GLOVE FOR OBTAINING A PATIENT'S BLOOD PRESSURE, PULSE AND OXYGEN SATURATION

(76) Inventor: Gregory Hays, Onsted, MI (US)

(*) Notice: Subject to any disclaimer, the term of this patent is extended or adjusted under 35 U.S.C. 154(b) by 0 days.

(21) Appl. No.: 13/419,067

(22) Filed: Mar. 13, 2012

(51) Int. Cl.
| A61B 5/024 | (2006.01) |
| A61B 5/00 | (2006.01) |
| A61B 5/022 | (2006.01) |
| A61B 5/0205 | (2006.01) |
| A61B 5/02 | (2006.01) |
| A61B 5/1455 | (2006.01) |
| A61B 5/021 | (2006.01) |

(52) U.S. Cl.
CPC .............. *A61B 5/02* (2013.01); *A61B 5/14551* (2013.01); *A61B 5/6806* (2013.01); *A61B 5/021* (2013.01); *A61B 5/02055* (2013.01); *A61B 5/1455* (2013.01); *A61B 5/6826* (2013.01)

(58) Field of Classification Search
None
See application file for complete search history.

(56) References Cited

U.S. PATENT DOCUMENTS

| 206,474 | A | * | 7/1878 | Morel ............................. 601/15 |
| 4,230,127 | A | * | 10/1980 | Larson ........................... 600/519 |
| 4,510,939 | A | | 4/1985 | Brenman et al. |
| 4,583,547 | A | | 4/1986 | Granek et al. |
| 4,662,378 | A | * | 5/1987 | Thomis ........................ 600/382 |
| 5,431,170 | A | | 7/1995 | Mathews |
| 5,511,546 | A | * | 4/1996 | Hon ............................... 600/490 |
| 5,670,944 | A | * | 9/1997 | Myllymaki ................. 340/573.1 |
| 5,734,625 | A | * | 3/1998 | Kondo ............... A61B 5/02438 368/10 |
| 5,738,104 | A | * | 4/1998 | Lo ...................... A61B 5/02438 600/509 |
| 5,771,891 | A | | 6/1998 | Gozani |
| 6,162,185 | A | * | 12/2000 | Amano et al. ................. 600/557 |
| 6,224,548 | B1 | * | 5/2001 | Gopinathan et al. ........... 600/300 |
| 6,248,064 | B1 | * | 6/2001 | Gopinathan et al. ........... 600/300 |
| 6,261,235 | B1 | * | 7/2001 | Amano et al. ................. 600/485 |
| 6,319,205 | B1 | * | 11/2001 | Goor ................... A61B 5/02007 600/481 |

(Continued)

FOREIGN PATENT DOCUMENTS

| EP | 1.522.256 | 4/2005 |
| WO | WO01/78592 | 10/2001 |

OTHER PUBLICATIONS

Gopinathan G., The EKG Glove, NYU Medical Center Presentation, Retrieved with the Wayback Machine from Jun. 10, 2010.*

*Primary Examiner* — Gary Jackson
*Assistant Examiner* — Manolis Pahakis
(74) *Attorney, Agent, or Firm* — Michael I. Kroll (57) ABSTRACT

A medical glove for obtaining a patient's blood pressure, pulse and oxygen saturation comprises a glove body for covering a hand of a medical practitioner. The glove body has a palm portion, a backhand portion, a thumb sheath, an index finger sheath and a middle finger sheath having memory with a clock for retrieval of stored and timed vital signs. A digital display module incorporating memory storage module and clock is on the backhand portion of the glove body. A first mechanism is between the middle finger sheath and the index finger sheath of the glove body, for measuring blood pressure of the patient to be indicated on the digital display module and storing the sensor data in memory for future retrieval. A second mechanism is between the thumb sheath and the index finger sheath of the glove body, for measuring oxygen saturation of the patient to be indicated on the digital display module and storing the sensor data in memory for future retrieval. A third mechanism is between the thumb sheath and the index finger sheath of the glove body for measuring the pulse of the patient to be indicated on the digital display module and storing the sensor data in memory for future retrieval.

6 Claims, 8 Drawing Sheets

(56) References Cited

U.S. PATENT DOCUMENTS

| | | | |
|---|---|---|---|
| 6,322,515 B1* | 11/2001 | Goor et al. | 600/485 |
| 6,361,501 B1* | 3/2002 | Amano | A61B 5/02028 600/485 |
| 6,432,060 B1* | 8/2002 | Amano | 600/490 |
| 6,443,906 B1* | 9/2002 | Ting et al. | 600/490 |
| 6,470,199 B1* | 10/2002 | Kopotic et al. | 600/344 |
| 6,475,153 B1* | 11/2002 | Khair et al. | 600/485 |
| 6,516,289 B2* | 2/2003 | David | 600/384 |
| 6,533,729 B1* | 3/2003 | Khair et al. | 600/503 |
| 6,540,673 B2* | 4/2003 | Gopinathan et al. | 600/300 |
| 6,589,171 B2* | 7/2003 | Keirsbilck | 600/300 |
| 6,595,918 B2* | 7/2003 | Gopinathan et al. | 600/300 |
| 6,646,552 B1* | 11/2003 | Lippert | 340/572.1 |
| 6,757,556 B2* | 6/2004 | Gopinathan et al. | 600/372 |
| 6,821,255 B2* | 11/2004 | Amano | 600/500 |
| 6,842,722 B2* | 1/2005 | David | 702/189 |
| 6,930,608 B2* | 8/2005 | Grajales et al. | 340/573.5 |
| 7,010,352 B2* | 3/2006 | Hogan | 607/48 |
| 7,089,061 B2* | 8/2006 | Grey | 607/63 |
| 7,112,175 B2* | 9/2006 | Gopinathan et al. | 600/508 |
| D544,961 S* | 6/2007 | Brady et al. | D24/167 |
| 7,300,406 B2* | 11/2007 | Carter | 600/528 |
| 7,306,563 B2* | 12/2007 | Huang | 600/500 |
| 7,435,222 B2* | 10/2008 | Gopinathan et al. | 600/508 |
| 7,654,962 B2* | 2/2010 | Sullivan | 600/481 |
| 7,670,263 B2* | 3/2010 | Ellis et al. | 482/8 |
| 7,683,759 B2* | 3/2010 | Martis et al. | 340/5.83 |
| 7,753,845 B2* | 7/2010 | Gopinathan et al. | 600/300 |
| 7,758,526 B2* | 7/2010 | DeGould | 602/21 |
| 7,993,275 B2* | 8/2011 | Banet et al. | 600/485 |
| 8,001,620 B2* | 8/2011 | Merkle et al. | 2/161.6 |
| 8,276,215 B2* | 10/2012 | Merkle et al. | 2/161.6 |
| 8,286,643 B2* | 10/2012 | Li et al. | 132/73 |
| 2002/0065471 A1* | 5/2002 | Amano | A61B 5/021 600/485 |
| 2002/0111777 A1* | 8/2002 | David | A61B 5/4041 702/189 |
| 2004/0019261 A1* | 1/2004 | Gopinathan et al. | 600/300 |
| 2005/0070824 A1* | 3/2005 | Rhad | A61B 5/1106 600/595 |
| 2007/0167844 A1* | 7/2007 | Asada et al. | 600/485 |
| 2008/0266118 A1* | 10/2008 | Pierson | A61B 5/0205 340/573.6 |
| 2010/0210956 A1* | 8/2010 | Im | 600/490 |
| 2011/0004074 A1* | 1/2011 | V et al. | 600/301 |
| 2011/0224530 A1 | 9/2011 | David et al. | |
| 2013/0013331 A1* | 1/2013 | Horseman | G06F 19/3418 705/2 |
| 2014/0330087 A1* | 11/2014 | Succi | A61B 8/06 600/301 |

* cited by examiner

OXYGEN SATURATION (FINGER)

OXYGEN SATURATION (EARLOBE)

FIG. 8

MEDICAL GLOVE FOR OBTAINING A PATIENT'S BLOOD PRESSURE, PULSE AND OXYGEN SATURATION

BACKGROUND OF THE INVENTION

1. Field of the Invention

The present invention relates generally to medical devices and, more specifically to a medical glove incorporating means for performing a plurality of medical diagnostic procedures on a patient that normally requires a separate device for each procedure.

As an example, blood pressure is measured through applying a cuff to a patient's upper arm, then using a stethoscope to listen for Korotkoff sounds to determine the systolic blood pressure and the diastolic blood pressure.

The present invention provides a blood pressure acquisition method obtained in a unique way by placing the middle finger with a fluid-filled reservoir over the radial artery, then applying enough pressure to obliterate the pulse. The index finger, equipped with a microphone or other sensor, is placed over the artery at a point just distal to the middle finger. The pressure applied by the middle finger is gradually released until the first Korotkoff sound is detected on the sensor. This then triggers the display of the pressure from the transducer at that point which corresponds to the systolic blood pressure. The middle finger pressure is gradually released until no pulse ($5^{th}$ Korotkoff sound) is detected in the sensor which corresponds to the diastolic pressure. The display is then triggered to display the pressure from the transducer. The pressure transducer is of the type used in invasive blood pressure monitoring systems and thus allows for the potential of continuous monitoring.

Additionally, the present invention provides a digital display module having memory and clock for storing real time sensor data that can be retrieved when desired.

2. Description of the Prior Art

While there are devices designed for obtaining a patient's physiological data that may be suitable for the purposes for which they were designed, they would not be as suitable for the purposes of the present invention, as hereinafter described.

SUMMARY OF THE PRESENT INVENTION

A primary object of the present invention is to provide a medical glove for measuring a patient's physiological/vital statistics.

Another object of the present invention is to provide a medical glove for detecting a patient's physiological statistics taken from the group of blood pressure, pulse and oxygen saturation.

Yet another object of the present invention is to provide a medical glove for encompassing a human hand having a palm portion and a back hand portion with finger sheaths extending therefrom.

Still yet another object of the present invention is to provide a medical glove having a digital display module positioned on a wrist band at the back hand portion of the glove.

An additional object of the present invention is to provide a medical glove wherein the digital display module has a housing incorporating a pressure transducer, analog to digital converter amplifier in the digital display module.

A further object of the present invention is to provide a medical glove for detecting a patient's physiological statistics having a fluid reservoir positioned preferably on the finger-sheath tip interior side in conduit communication with the pressure transducer.

A yet further object of the present invention is to provide a medical glove for detecting a patient's physiological statistics wherein the reservoir contains saline or other fluid.

A still yet further object of the present invention is to provide a medical glove for detecting a patient's physiological statistics wherein the fluid reservoir finger sheath is preferably the glove sheath for the middle finger.

Another object of the present invention is to provide a medical glove for detecting a patient's physiological statistics having a microphone/sensor positioned preferably on the finger-sheath tip interior side in electrical communication with the amplifier.

Yet another object of the present invention is to provide a medical glove for detecting a patient's physiological statistics wherein the microphone/sensor finger sheath is preferably the glove sheath for the index finger.

Still yet another object of the present invention is to provide a medical glove for detecting a patient's physiological statistics having an oxygen saturation/pulse transmitter and an oxygen saturation/pulse sensor, located on juxtapositioned finger sheath tips in electrical communication with the digital display module.

Another object of the present invention is to provide a medical glove, within the oxygen saturation/pulse transmitter finger sheath is preferably for the index finger, while there oxygen saturation/pulse sensor finger sheath is preferably for the thumb.

Yet another object of the present invention is to provide a medical glove digital display module incorporating memory and clock for storing historical sensor data for future retrieval.

Additional objects of the present invention will appear as the description proceeds.

The present invention overcomes the shortcomings of the prior art by providing a medical glove for acquiring and storing a patients physiological data within a digital display module positioned on the back hand portion in communication with a plurality of components and sensors positioned approximate the finger sheath tips.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Turning now descriptively to the drawings, in which similar reference characters denote similar elements throughout the several views, the Figures illustrate the medical glove of the present invention. With regard to the reference numerals used, the following numbering is used throughout the various drawing figures.

10 medical glove
12 digital display module on wrist band 14
14 wrist band on glove 10
16 fluid filled reservoir in middle finger sheath 18
18 middle finger sheath of glove 10
20 pressure transducer in digital display module 12
22 microphone/sensor in index finger sheath 24
24 index finger sheath of glove 10
26 oxygen saturation sensor in thumb sheath 28
28 thumb sheath of glove 10
30 oxygen saturation transmitter in index finger sheath 24
32 finger
34 earlobe
36 analog to digital converter amplifier in digital display module 12
38 clock of 12
40 pressure switch in oxygen transmitter 30
42 memory of 12

DETAILED DESCRIPTION OF THE PREFERRED EMBODIMENT

The following discussion describes in detail one embodiment of the invention. This discussion should not be construed, however, as limiting the invention to those particular embodiments, practitioners skilled in the art will recognize numerous other embodiments as well. For definition of the complete scope of the invention, the reader is directed to appended claims.

Figure 1:
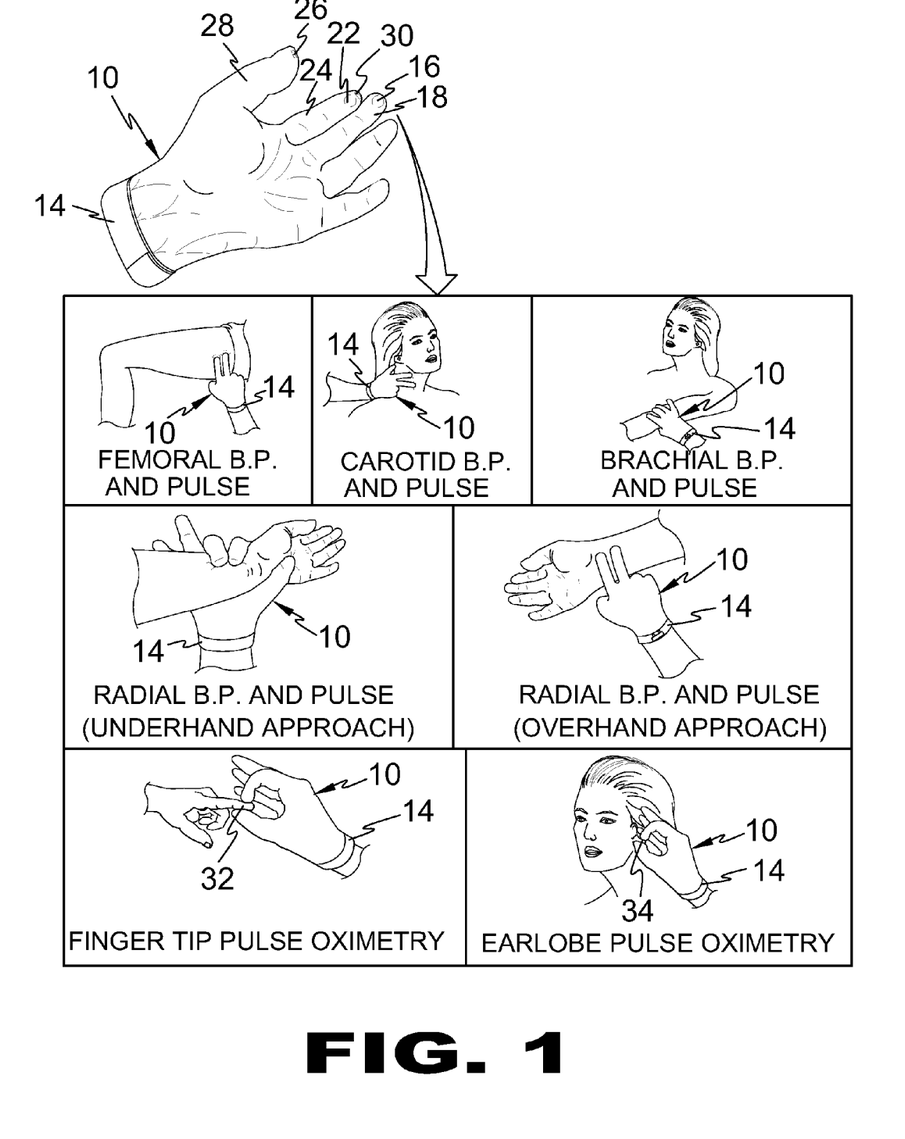
FIG. 1 is an illustrative view of the present invention and uses.

Referring to FIG. 1, shown is an illustrative view of the present invention and uses. The present invention is a medical glove 10 designed to obtain blood pressure, pulse and oxygen saturation via the use of all components and sensors sewn into the finger tips. A digital display module 12 will be attached to a wrist band 14 using a removable attachment (not shown). The medical glove 10 allows vital signs to be obtained in a fraction of the time, making the medical glove 10 very useful for emergency applications, eliminating the need to carry multiple pieces of equipment. Also incorporated into the digital display module is memory and clock enabling the storage and retrieval of historical sensor data.

Figure 2:
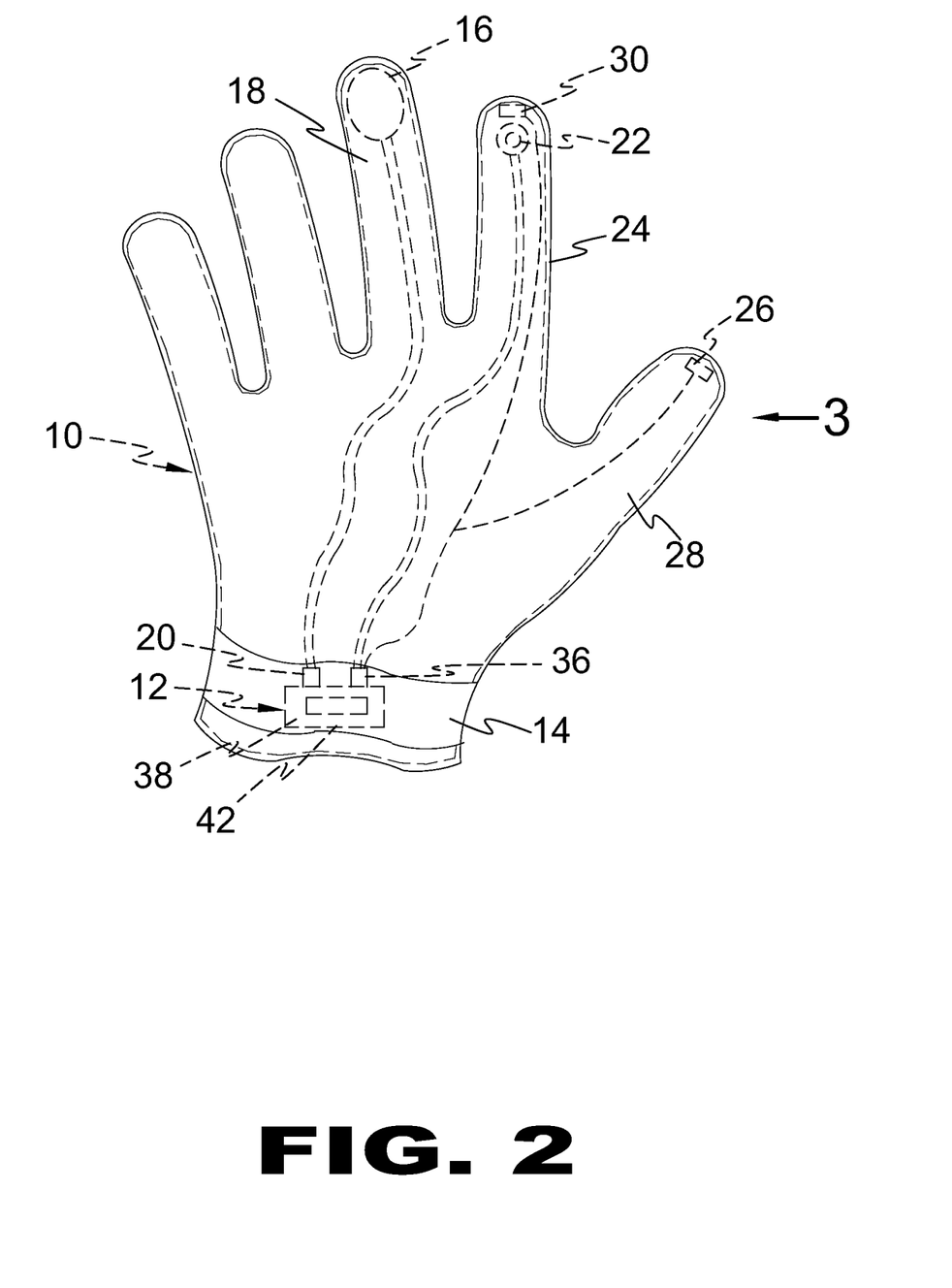
FIG. 2 is a diagrammatic front view of the present invention, with the various components in phantom.

Referring to FIG. 2, shown is a diagrammatic front view of the present invention with the various components in phantom. The medical glove 10 of the present invention is designed to obtain blood pressure, pulse and oxygen saturation through the various components and sensors sewn into the finger tips. The digital display module 12 is attached to the wrist band 14 via the removable attachment (not shown). The blood pressure acquisition method is completely unique in that it does not employ a circumferential band or pulse wave transit time. A fluid filled reservoir 16 is sewn into the tip of a middle finger sheath 18 to compress the artery using digital pressure. The pressure is released gradually and a connected pressure transducer 20 reads the value directly by a microphone/sensor 22 sewn into an index finger sheath 24, detecting pulse sounds that are sent to the digital display module 12 on the wrist band 14, thereby recording blood pressure and pulse. The oxygen saturation is obtained by a sensor 26 in a thumb sheath 28 and a transmitter 30 in the index finger sheath 24. The thumb and index finger sheaths 28, 24 grip either a finger 32, a toe (not shown) or an earlobe 34 to obtain oxygen saturation and pulse. Also incorporated into the digital display module is a data storage module comprising at least one memory module 42 and clock 38 thereby enabling the storage and retrieval of historical sensor data.

Figure 3:
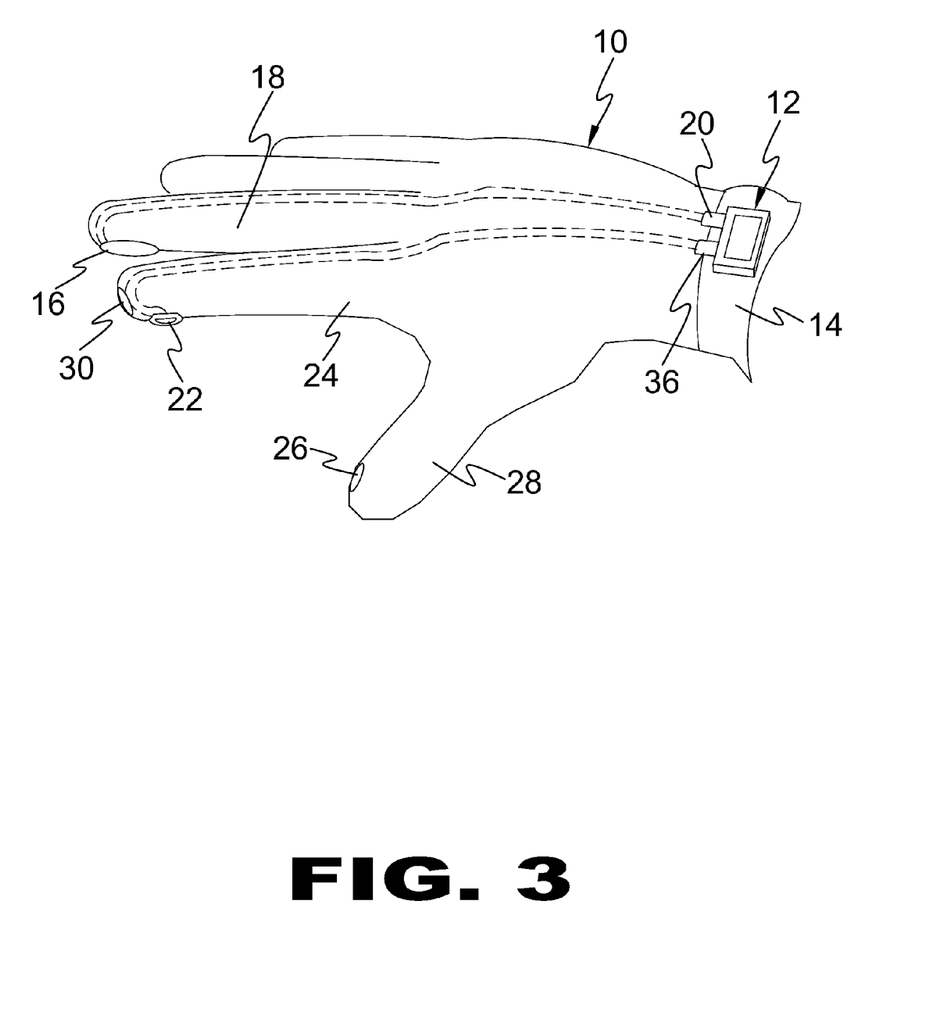
FIG. 3 is a diagrammatic side view taken in the direction for arrow 3 in FIG. 2.

Referring to FIG. 3, shown is a diagrammatic side view taken in the direction for arrow 3 in FIG. 2. The medical glove 10 of the present invention is designed to obtain blood pressure, pulse and oxygen saturation through components and sensors sewn into the finger tips. The digital display module 12 is attached to the wrist band 14 via the removable attachment (not shown). The blood pressure acquisition method is completely unique in that it does not employ a circumferential band or pulse wave transit time. The fluid filled reservoir 16 is sewn into the tip of the middle finger sheath 18 to compress the artery using digital pressure. The pressure is released gradually and the connected pressure transducer 20 reads the value directly by the microphone/sensor 22 sewn into the index finger sheath 24 detecting pulse sounds that are sent to the digital display module 12 on the wrist band 14, thereby recording blood pressure and pulse. The oxygen saturation is obtained by the sensor 26 in the thumb sheath 28 and the transmitter 30 in the index finger sheath 24. The thumb and index finger sheaths 28, 24 grip either the finger 32, toe (not shown) or earlobe 34 to obtain oxygen saturation and pulse.

Figure 4:
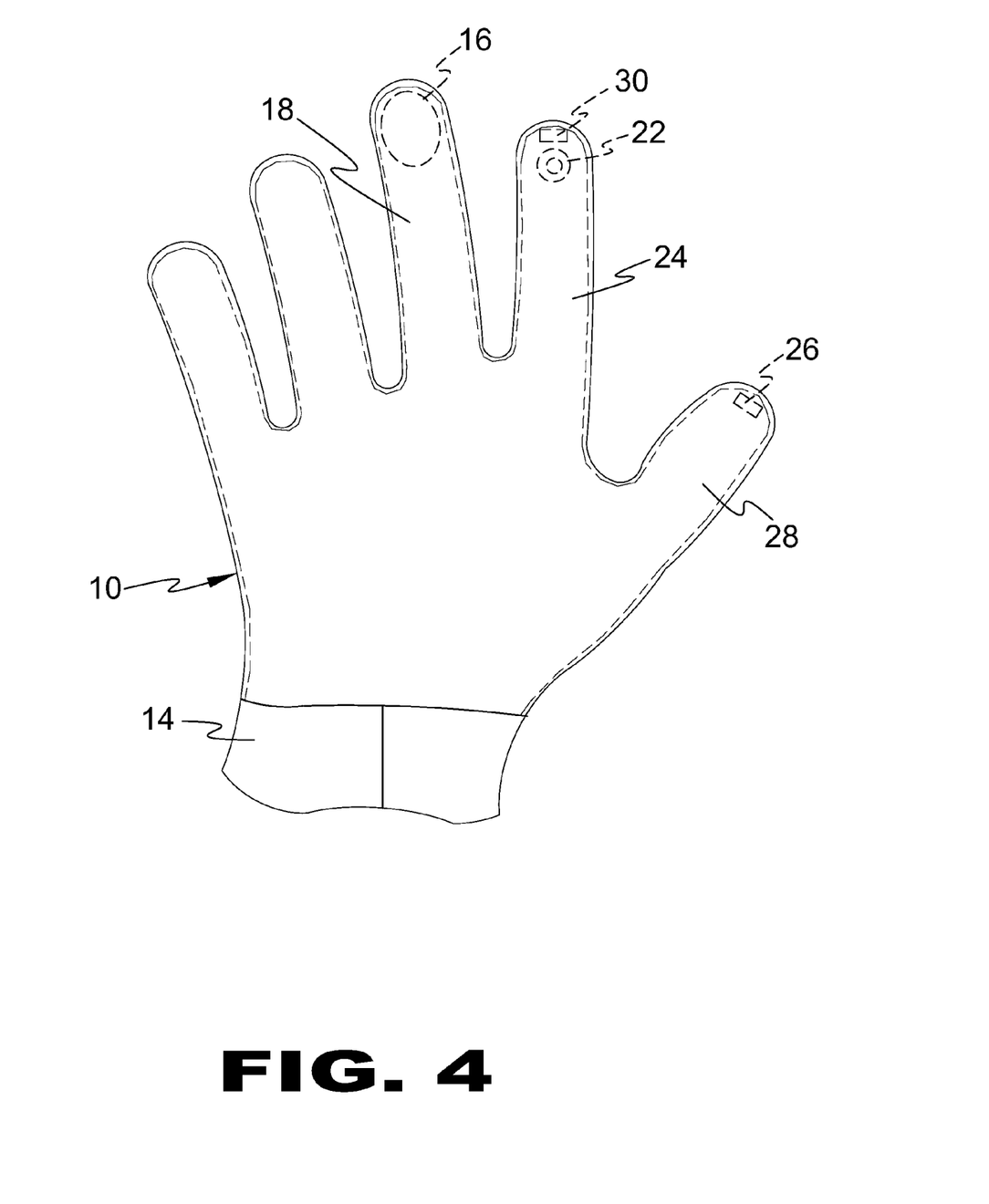
FIG. 4 is another diagrammatic front view of the of the present invention.

Referring to FIG. 4, shown is another diagrammatic front view of the present invention. The fluid filled reservoir 16 positioned on the top portion of the middle finger sheath 18 is used in conjunction with the microphone/sensor 22 positioned on the top portion of the index finger sheath 24 to acquire the systolic blood pressure, the diastolic blood pressure and pulse. The index finger sheath 24 also incorporates an oxygen saturation transmitter 30 approximate the tip with an oxygen saturation sensor 26 incorporated into the tip of the thumb sheath 28, that when used in conjunction through pressure on the finger 32, toe (not shown) or earlobe 34, provides oxygen saturation through an analog to digital converter amplifier 36 forming an integral part of the digital display module 12.

Figure 5:
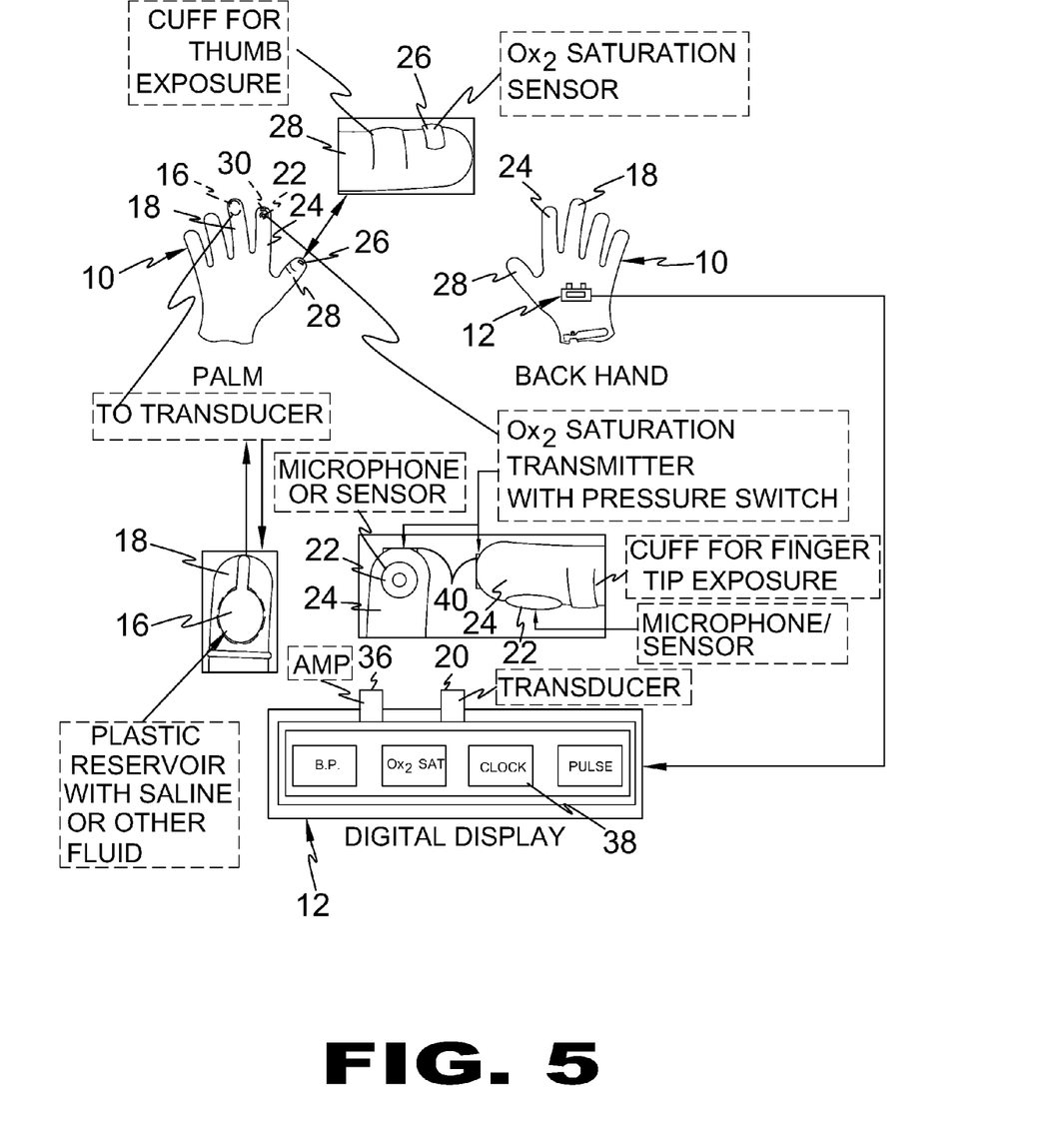
FIG. 5 is a diagrammatic chart of the present invention.

Referring to FIG. 5, shown is a diagrammatic chart of the present invention. The medical glove 10 incorporates means for obtaining a patient's vital signs through a single medical instrument as opposed to using several medical instruments. The acquisition procedure is also simplified since ambient noise can interfere with the use of a stethoscope in determining systolic and diastolic pressure readings. Furthermore, the medical glove 10 is compact making it medical practitioner friendly and less traumatic to users by negating the need for a cuff to occlude blood flow in a patient's arm and a stethoscope to listen for the Korotkoff sounds to determine the systolic blood pressure and the diastolic blood pressure.

Figure 6:
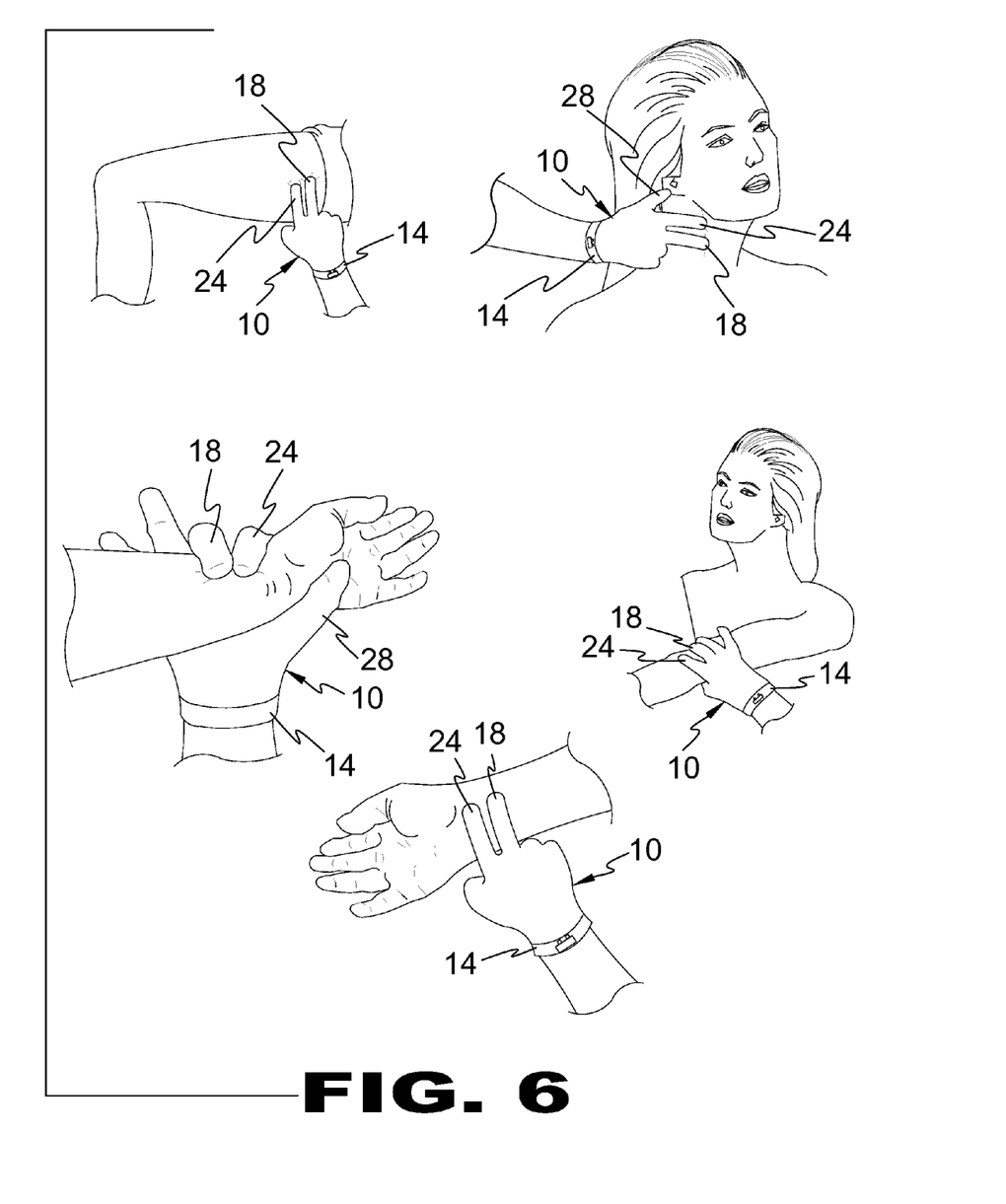
FIG. 6 is a diagrammatic perspective view of examples of the present invention in use.

Referring to FIG. 6, shown is diagrammatic perspective view of examples of the present invention in use. The blood pressure acquisition method is completely unique in that it does not employ a circumferential band or pulse wave transit time. The fluid filled reservoir 16 is positioned in the middle finger sheath 18 approximate the tip where compression is applied to the artery using digital pressure. The pressure is released gradually and the connected pressure transducer 20 reads the value directly.

Figure 7:
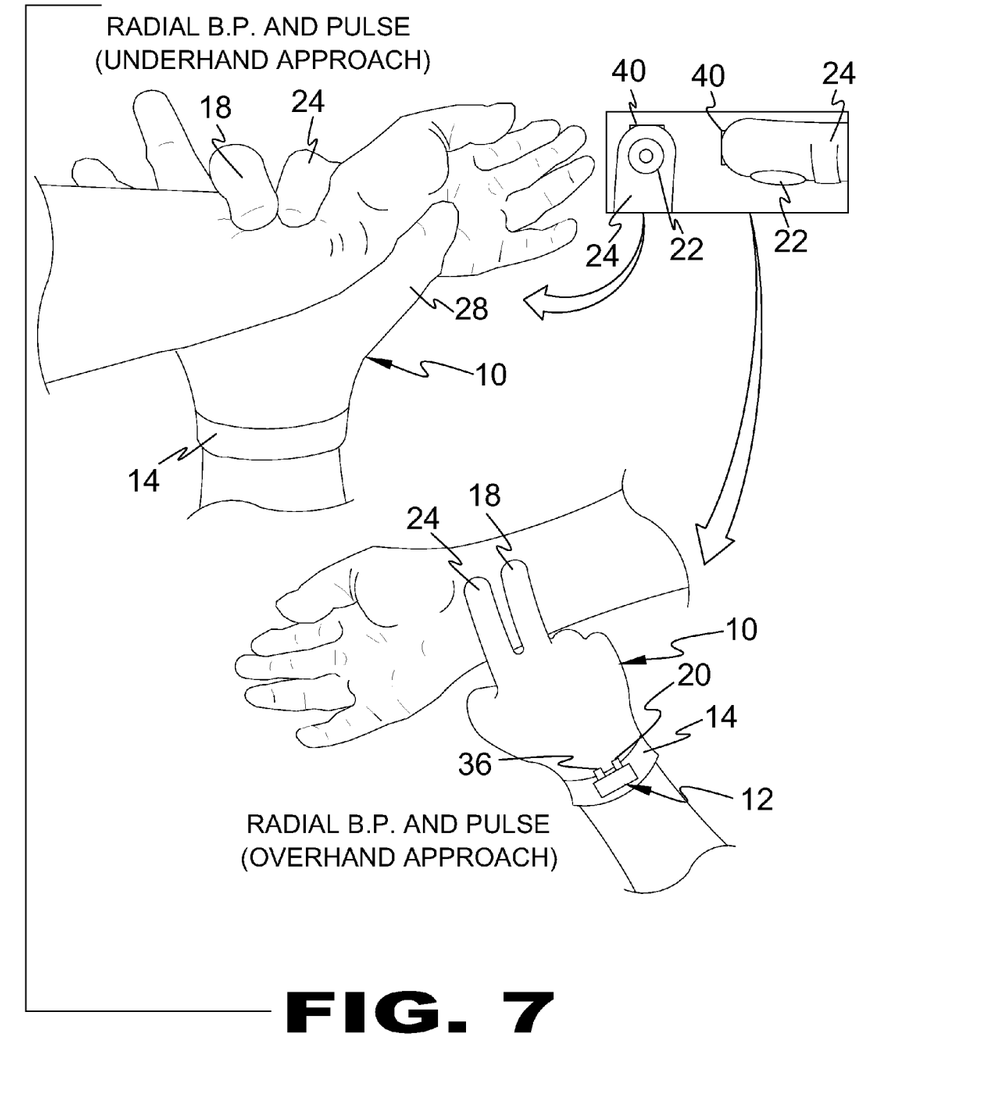
FIG. 7 is a diagrammatic perspective view of examples of the present invention in use.

Referring to FIG. 7, shown is a diagrammatic perspective view of examples of the present invention in use. The pulse detection is accomplished by two mechanisms: a clock 38 which times the impulses sent from the microphone/sensor 22 in the index finger sheath 24 to the digital display module 12 and a pulse override that is actuated by a pressure switch 40 in the oxygen transmitter 30. This causes the digital display module 12 to display the pulse obtained from the oxygen sensor 26 (pulse sensing is a standard in all oxygen sensors) rather than await a signal from the microphone/sensor 22. This allows for a more accurate pulse due to a longer sampling interval and allows for continuous pulse detection if needed.

Figure 8:
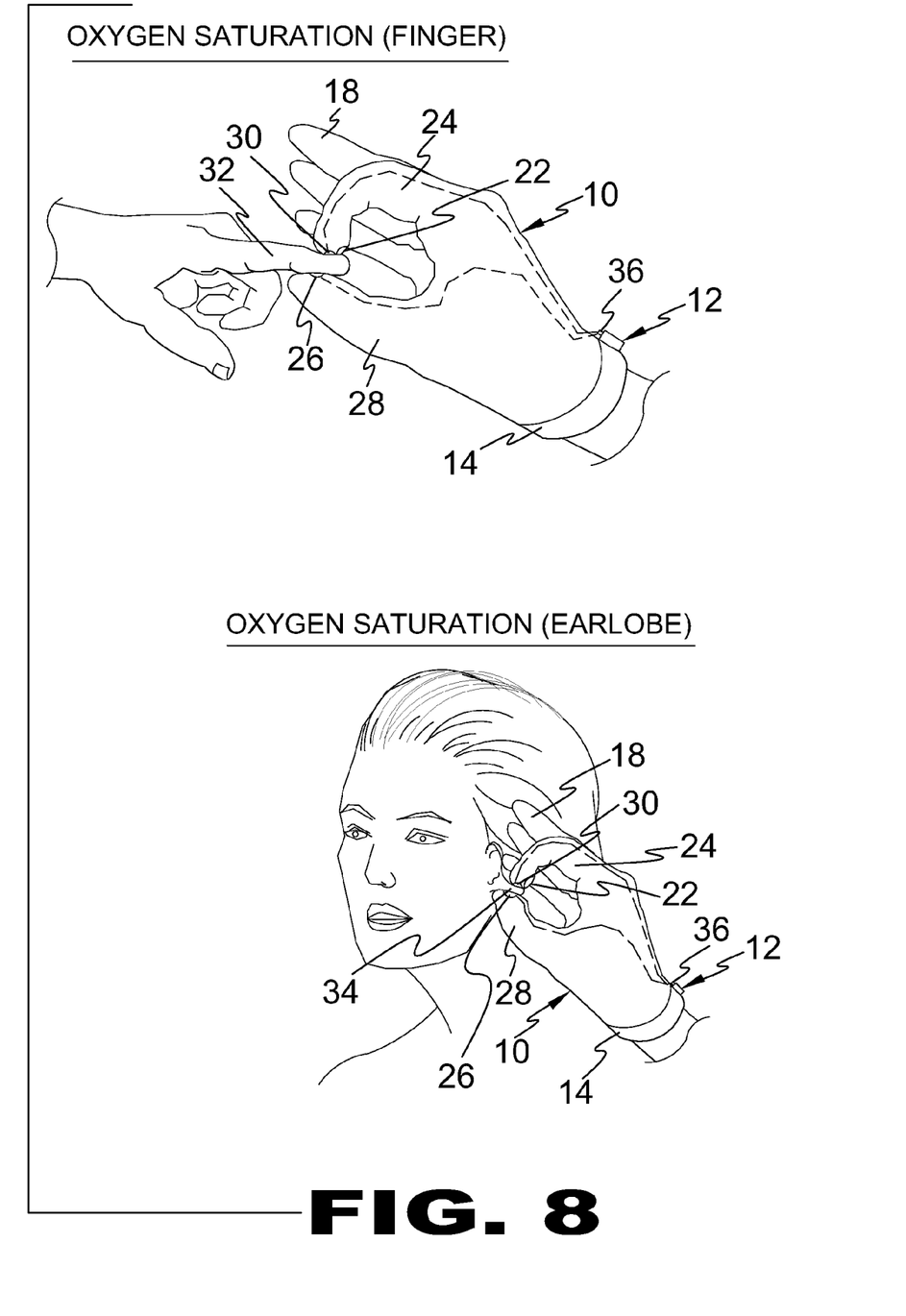
FIG. 8 is a diagrammatic perspective view of examples of the present invention in use.

Referring to FIG. 8, shown is a diagrammatic perspective view of examples of the present invention in use. The oxygen saturation is obtained by the sensor 26 in the thumb sheath 28 and the transmitter 30 index finger sheath 24. The thumb sheath 28 and the index finger sheath 34 are then opposed over the finger 32, toe (not shown) or earlobe 24.

What is claimed is:

1. A medical glove for obtaining a patient's blood pressure, pulse and oxygen saturation which comprises:
    a glove body for covering a hand of a medical practitioner, the glove body having a palm portion, a backhand portion, a thumb sheath, an index finger sheath and a middle finger sheath;
    a fluid filled reservoir incorporated on a tip of said middle finger sheath and arranged to compress an artery of the patient;
    a microphone incorporated on a tip of said index finger sheath and arranged to detect a pulse sound from the artery of the patient as pressure is released gradually by said middle finger sheath;
    an oxygen saturation sensor in said thumb sheath and an oxygen saturation transmitter on the tip of the index finger sheath configured to measure oxygen saturation and pulse of the patient, and a pressure switch in the oxygen saturation transmitter;
    a pressure transducer connected to the microphone and the fluid filled reservoir;
    a digital display module on the backhand portion of the glove body configured to display the blood pressure, pulse and oxygen saturation of the patient based on signals from the fluid filled reservoir, the microphone, the oxygen saturation sensor and the oxygen saturation transmitter, wherein the pressure switch is configured to override the microphone and cause the digital display module to display the pulse based on the oxygen saturation transmitter, wherein the digital display module has a clock and a memory for storing historical blood pressure, pulse, and oxygen saturation data for future retrieval.

2. The medical glove as recited in claim 1, wherein:
    the pressure transducer is on the digital display module; and
    an analog to digital converter amplifier is on the digital display module and is electrically connected to the microphone.

3. The medical glove as recited in claim 2, wherein the oxygen saturation sensor and the oxygen transmitter are electrically connected to the analog to digital converter amplifier on the digital display module.

4. The medical glove as recited in claim 3, wherein the digital display module is electrically connected to the analog to digital converter amplifier.

5. The medical glove as recited in claim 3, wherein the oxygen saturation measuring sensor comprises a pulse oximeter unit.

6. The medical glove as recited in claim 5, wherein the pulse oximeter unit comprises:
    a) two light emitting diodes at 600 nm and 940 nm retained within the index finger sheath; and
    b) two light collecting sensors retained within the thumb sheath, wherein the light collecting sensors are configured to measure an amount of red and infrared light emerging from tissues traversed by light rays, wherein the two light emitting diodes and the two light collecting sensors are electrically connected to the analog to digital converter amplifier on the digital display module.

* * * * *